US012306086B2

(12) United States Patent
Matsushita et al.

(10) Patent No.: US 12,306,086 B2
(45) Date of Patent: May 20, 2025

(54) METHOD FOR DISPLAYING CELL COUNT INFORMATION, SYSTEM, AND COMPUTER-READABLE MEDIUM

(71) Applicant: EVIDENT CORPORATION, Nagano (JP)

(72) Inventors: Akira Matsushita, Tokyo (JP); Yu Hirosawa, Tokyo (JP); Taiji Mine, Tokyo (JP); Takuma Dezawa, Tokyo (JP)

(73) Assignee: Evident Corporation, Nagano (JP)

(*) Notice: Subject to any disclaimer, the term of this patent is extended or adjusted under 35 U.S.C. 154(b) by 730 days.

(21) Appl. No.: 17/581,364

(22) Filed: Jan. 21, 2022

(65) Prior Publication Data

US 2022/0146404 A1 May 12, 2022

Related U.S. Application Data

(63) Continuation of application No. PCT/JP2019/045735, filed on Nov. 22, 2019.

(51) Int. Cl.
*G01N 15/1433* (2024.01)
*G01N 15/14* (2024.01)
(Continued)

(52) U.S. Cl.
CPC ..... *G01N 15/1433* (2024.01); *G01N 33/5094* (2013.01); *G01N 35/00069* (2013.01);
(Continued)

(58) Field of Classification Search
CPC .. G06V 10/7792; G06V 20/698; G06N 3/045; G06N 3/08; G06N 20/00;
(Continued)

(56) References Cited

U.S. PATENT DOCUMENTS

2003/0096324 A1   5/2003   Matveev et al.

FOREIGN PATENT DOCUMENTS

| CN | 107687999 A | * | 2/2018 |
| JP | 2005-502369 A | | 1/2005 |
| JP | 2006-349533 A | | 12/2006 |
| JP | 2007-048006 A | | 2/2007 |

OTHER PUBLICATIONS

Drury, Josephine A., et al. "Endometrial cell counts in recurrent miscarriage: a comparison of counting methods." Histopathology 59.6 (2011): 1156-1162. (Year: 2011).*

(Continued)

*Primary Examiner* — Vu Le
*Assistant Examiner* — Tracy Mangialaschi
(74) *Attorney, Agent, or Firm* — Scully, Scott, Murphy & Presser, P.C.

(57) ABSTRACT

A method for displaying cell count information includes steps for: obtaining a cell image; obtaining a first cell count output by applying the cell image to a first counting model; obtaining a second cell count output by applying the cell image to a second counting model; and displaying, on the basis of the first and second cell counts, a screen on which at least either of the first and second cell counts and a correlation between the first and second cell counts are visualized. The first counting model is different from the second counting model.

16 Claims, 19 Drawing Sheets

(51) Int. Cl.
 G01N 33/50 (2006.01)
 G01N 35/00 (2006.01)
 G06N 20/00 (2019.01)
 G06T 7/00 (2017.01)
(52) U.S. Cl.
 CPC .......... G06N 20/00 (2019.01); G06T 7/0012 (2013.01); *G01N 2015/1486* (2013.01); *G06T 2207/30024* (2013.01); *G06T 2207/30242* (2013.01)
(58) Field of Classification Search
 CPC .......... G01N 15/1433; G01N 15/1429; G01N 33/5094; G01N 35/00069; G01N 2015/1486; G01N 2015/1006; C12M 1/34; G06T 7/0012; G06T 2207/30242; G06T 2207/30024
 See application file for complete search history.

(56) References Cited

OTHER PUBLICATIONS

Piccinini, Filippo, et al. "Cell counting and viability assessment of 2D and 3D cell cultures: expected reliability of the trypan blue assay." Biological procedures online 19 (2017): 1-12. (Year: 2017).*
International Search Report dated Feb. 18, 2020 received in PCT/JP2019/045735.

* cited by examiner

METHOD FOR DISPLAYING CELL COUNT INFORMATION, SYSTEM, AND COMPUTER-READABLE MEDIUM

CROSS REFERENCE TO RELATED APPLICATIONS

This is a Continuation Application of PCT Application No. PCT/JP2019/045735, filed Nov. 22, 2019, which was not published under PCT Article 21(2) in English.

BACKGROUND OF THE INVENTION

Field of the Invention

Disclosures herein are related to a method for displaying cell count information, a system, and a computer-readable medium.

Description of the Related Art

Known cell counting methods include a method wherein a person counts the number of cells by using a cell counting slide, a method wherein the number of cells flowing in line is counted using a flow cytometer, and a method wherein an image of cells is analyzed to count the number of the cells in the image. The method that involves counting the number of cells in an image can be implemented even during culturing, so such a system is preferable for, for example, an application in which the number of cells in a culturing process is counted to monitor the culture state.

The method that involves counting the number of cells in an image is described in, for example, Japanese National Publication of International Patent Application No. 2005-502369. Japanese National Publication of International Patent Application No. 2005-502369 indicates that "various image processing methods such as binarization, background uniformization, normalization and filtering are performed to enhance the appearance of the cells in the investigational data to aid the process of cell counting."

SUMMARY OF THE INVENTION

A method in accordance with an aspect of the present invention is a method for displaying cell count information and includes steps for: obtaining a plurality of cell images generated by successively imaging cells; obtaining a first cell count output by applying the plurality of cell images to a first counting model, the first counting model being for counting a number of cells included in an image; obtaining a second cell count output by applying, to a second counting model, each of a plurality of cell images that are the same as the images for which the first cell count has been obtained, the second counting model being for counting a number of cells included in an image, and being different from the first counting model; and displaying, on the basis of the first and second cell counts, a screen on which at least either of the first and second cell counts and a correlation between the first and second cell counts are visualized.

A method in accordance with another aspect of the present invention is a method for displaying cell count information and includes steps for: obtaining a plurality of cell images generated by successively imaging cells; obtaining a first cell count output by applying each of the plurality of cell images to a first counting model, the first counting model being for counting a number of cells included in an image, and having a higher precision than a second counting model and a lower recall factor than the second counting model; obtaining a second cell count output by applying, to the second counting model, each of a plurality of cell images that are the same as the images for which the first cell count has been obtained, the second counting model being for counting a number of cells included in an image; and reporting an abnormality occurrence to a user when an abnormality in a culture environment is detected on the basis of a relationship between the first and second cell counts.

A system in accordance with an aspect of the present invention includes an electric circuit, and the electric circuit obtains, from an image capturing apparatus, a plurality of cell images generated by successively imaging cells; obtains a first cell count output by applying each of the plurality of cell images to a first counting model, the first counting model being for counting a number of cells included in an image, and having a higher precision than a second counting model and a lower recall factor than the second counting model; obtains a second cell count output by applying, to the second counting model, each of a plurality of cell images that are the same as the images for which the first cell count has been obtained, the second counting model being for counting a number of cells included in an image; and causes, on the basis of the first cell count and the second cell count, a display apparatus to display a screen on which at least either of the first and second cell counts and a correlation between the first and second cell counts are visualized.

A system in accordance with another aspect of the present invention includes an electric circuit, and the electric circuit obtains, from an image capturing apparatus, a plurality of cell images generated by successively imaging cells; obtains a first cell count output by applying each of the plurality of cell images to a first counting model, the first counting model being for counting a number of cells included in an image, and having a higher precision than a second counting model and a lower recall factor than the second counting model; obtains a second cell count output by applying, to the second counting model, each of a plurality of cell images that are the same as the images for which the first cell count has been obtained, the second counting model being for counting a number of cells included in an image; and reports an abnormality occurrence to a user when detecting an abnormality in a culture environment on the basis of a relationship between the first and second cell counts.

A non-transitory computer-readable medium in accordance with an aspect of the present invention has recorded therein a program for causing a computer to perform a process for: obtaining a cell image generated by imaging cells from an image capturing apparatus; inputting the cell image to a first counting model, the first counting model being for counting a number of cells included in an image, and having a higher precision than a second counting model and a lower recall factor than the second counting model; inputting the cell image to the second counting model, the second counting model being for counting a number of cells included in an image; and on the basis of a first cell count output by inputting the cell image to the first counting model and a second cell count output by inputting the cell image to the second counting model, displaying a screen on which at least either of the first and second cell counts and a correlation between the first and second cell counts are visualized.

BRIEF DESCRIPTION OF THE DRAWINGS

The present invention will be more apparent from the following detailed description when the accompanying drawings are referenced.

DESCRIPTION OF THE EMBODIMENTS

As a general rule, an operator of cell culturing understands a desirable temporal variation in a cell count and thus can detect when the temporal variation in the cell count is different from an expected one by monitoring the cell count during culturing. However, it is not easy to specify the cause of the detected abnormality.

In particular, it is very difficult to distinguish whether the deviation from the expected temporal variation results from a culture environment or variations in quality between cells or whether the deviation results from a fault in image recognition. Hence, every time an abnormality occurs, the cell image needs to be checked to distinguish the cause, thereby imposing a burden on the operator.

Although descriptions have been given by taking examples pertaining to cell culturing, the above technical problem may also arise in situations other than cell culturing, as long as the number of cells is counted using an image.

The following describes embodiments of the present invention.

Figure 1:
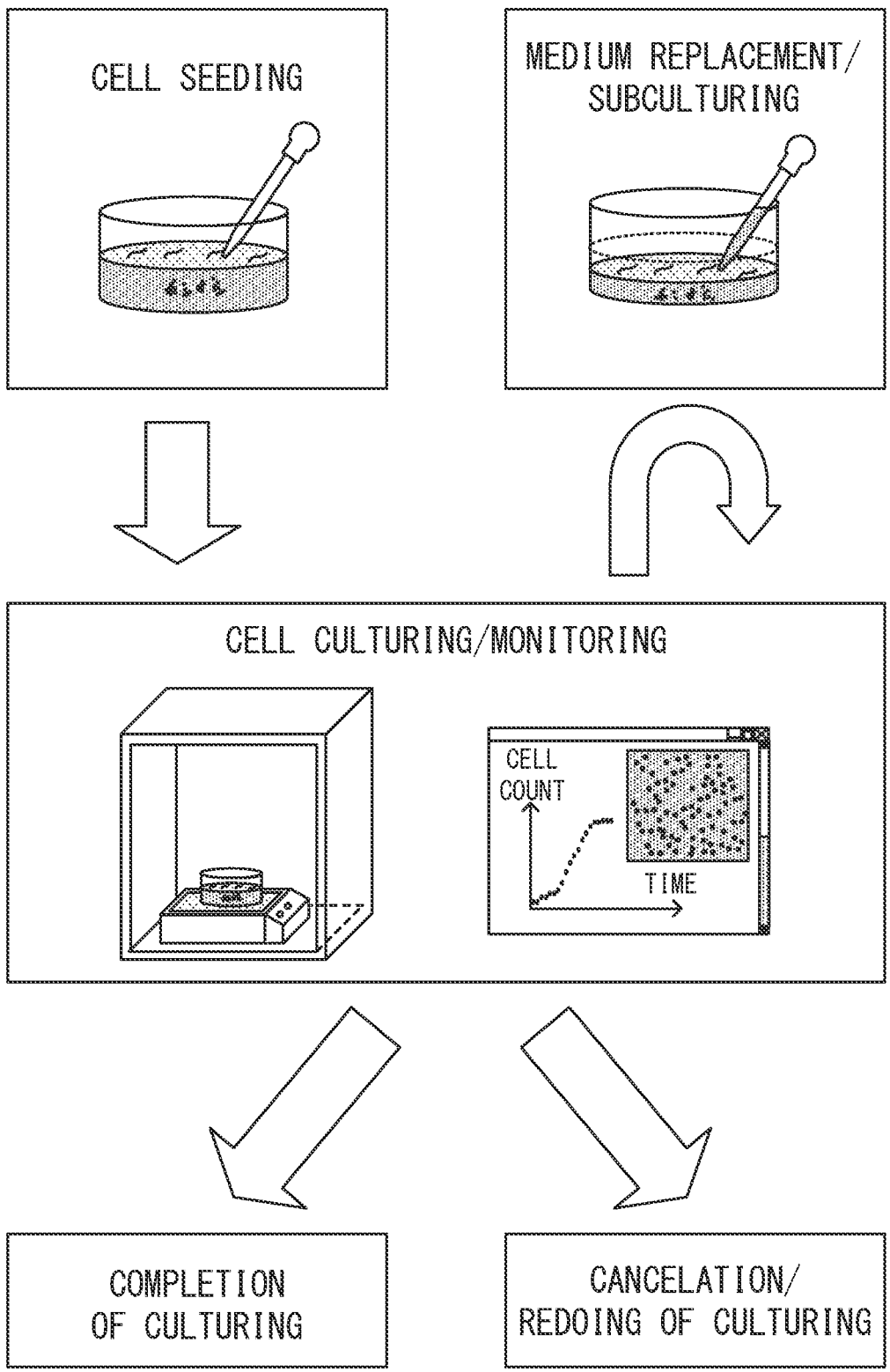
FIG. 1 is an explanatory diagram for a cell culturing procedure.

FIG. 1 is an explanatory diagram for a cell culturing procedure. By referring to FIG. 1, the following describes tasks performed by an operator in cell culturing for growing culture cells prepared in advance so as to reach a target number.

The operator first seeds culture cells within a culture container and then disposes the culture container on an image capturing apparatus within an incubator so as to start cell culturing. After the cell culturing starts, the operator monitors the cell culturing by checking a cell count obtained from a cell image obtained by the image capturing apparatus and checking the cell image according to need.

For example, directly after the start of culturing, the operator may determine, according to the cell count, whether the seeding density is appropriate, and make an adjustment to attain a seeding density recommended by a protocol. During a logarithmic growth phase, the operator may replace a culture medium at a frequency corresponding to a cell density obtained from the cell count. When the cell density is greater than a predetermined value, the operator may perform subculturing.

When determining according to the cell count and a cell image that cell culturing cannot be continued, the operator cancels or redoes the cell culturing. When determining that the number of culture cells has reached a target number owing to the smooth progress of cell culturing, the operator completes the cell culturing.

As described above, a cell count may be used as a trigger to perform various tasks in cell culturing, so the cell count in cell culturing and the temporal variation therein are deemed as important information for successfully performing the cell culturing.

As indicated above, the number of cells is desirably counted using an image so as to obtain a cell count while continuing cell culturing. However, there is still room for improvement in the reliability of a cell count obtained through image analysis. In cell culturing performed to provide a target number of cells, it is undesirable to count, as the number of desired cells, the number of non-cell matters, e.g., motes or dusts, dead cells, or cells of a type not to be subjected to counting, because an overestimated cell count could be mistakenly obtained. Thus, it is considered that a counting model for assessing cells in accordance with a higher standard is preferable when monitoring cell culturing.

However, such a counting model is generally sensitive to a change in the shape of cells that could occur in a culturing process, so the cell count obtained from the counting model is likely to exhibit an abnormal temporal variation that is different from the actual temporal variation in the cell count. The change in a shape herein may be a change in the shape resulting from an actual deformation of cells or may be a visual change in the shape of cells that is seen in an image due to, for example, multi-layering of the cells. In the case of a model with a strict standard for assessment, for example, when the shape of cells changes even only a little, it may be assessed that the standard shape in the counting model is not provided, and the number of the cells may not be counted. In particular, if an image presents a shape that happens to be different from the standard shape in the counting model due to, for example, multi-layering of cells, the counted number could be smaller than the actual cell count. All of the changes in shapes are the same in that none of the changes are an abnormal event in cell culturing.

Accordingly, counting models typically expected to be used for the monitoring of cell culturing generally provide a reliable cell count that is non-overestimated owing to a high standard for assessment, but may possibly cause an abnormal temporal variation in a cell count due to a normal event that could occur in the culturing process. It is difficult to distinguish, according to only the cell count output from the counting model, whether the abnormal temporal variation, or the deviation from the expected temporal variation, is a true abnormality resulting from a culture environment or a false abnormality resulting from a fault in image recognition pertaining to the counting model.

In consideration of the characteristics of the above-described counting model used in cell culturing, the following describes a method for allowing for distinction between a true abnormality and a false abnormality. In this technique, a user does not need to check an image so as to implement the distinction. However, image-based checking may also be performed in this technique.

Figure 2:
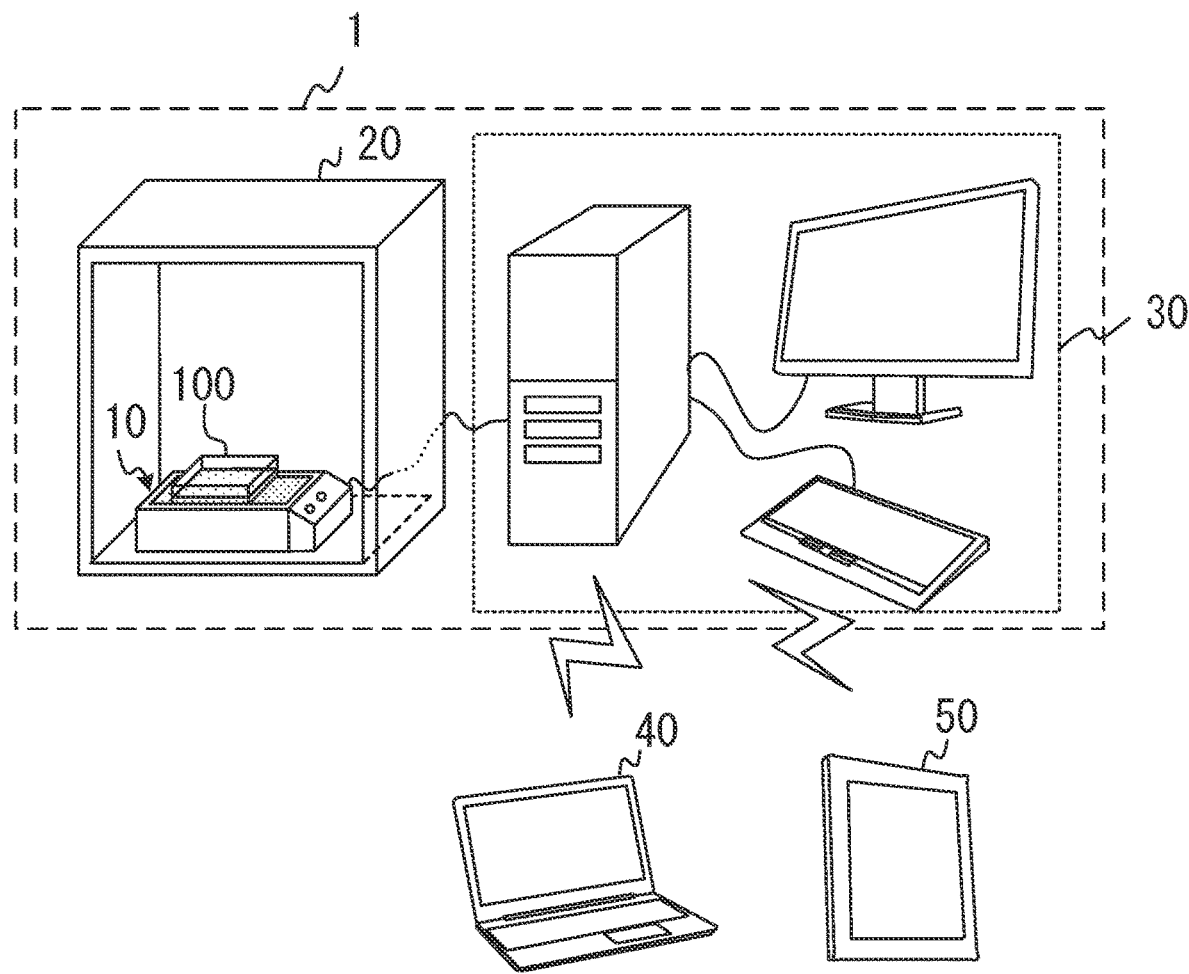
FIG. 2 exemplifies the configuration of a cell culture monitoring system.
Figure 3:
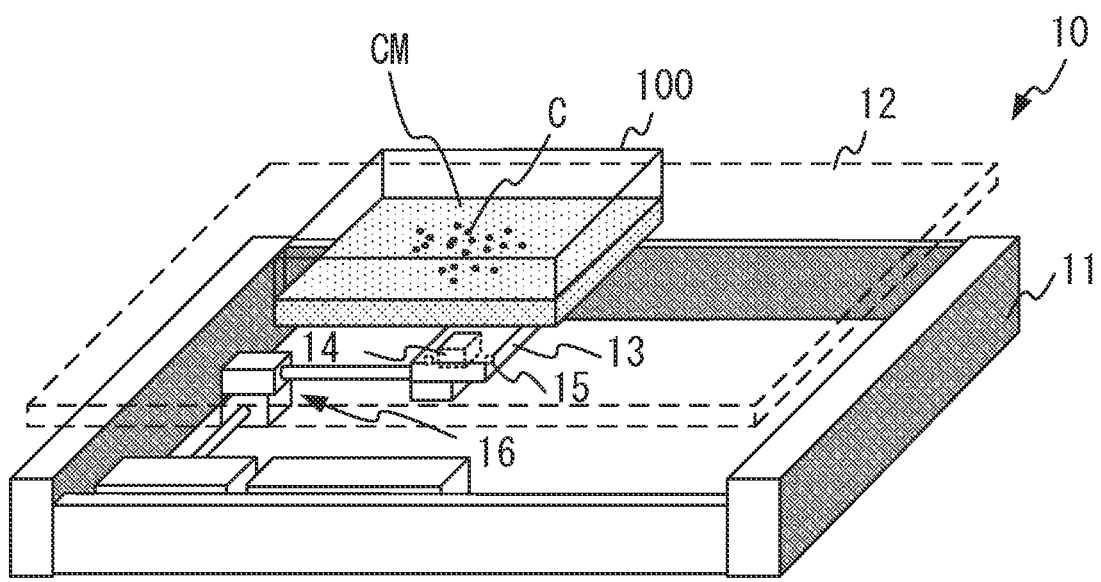
FIG. 3 exemplifies the configuration of an image capturing apparatus.
Figure 4:
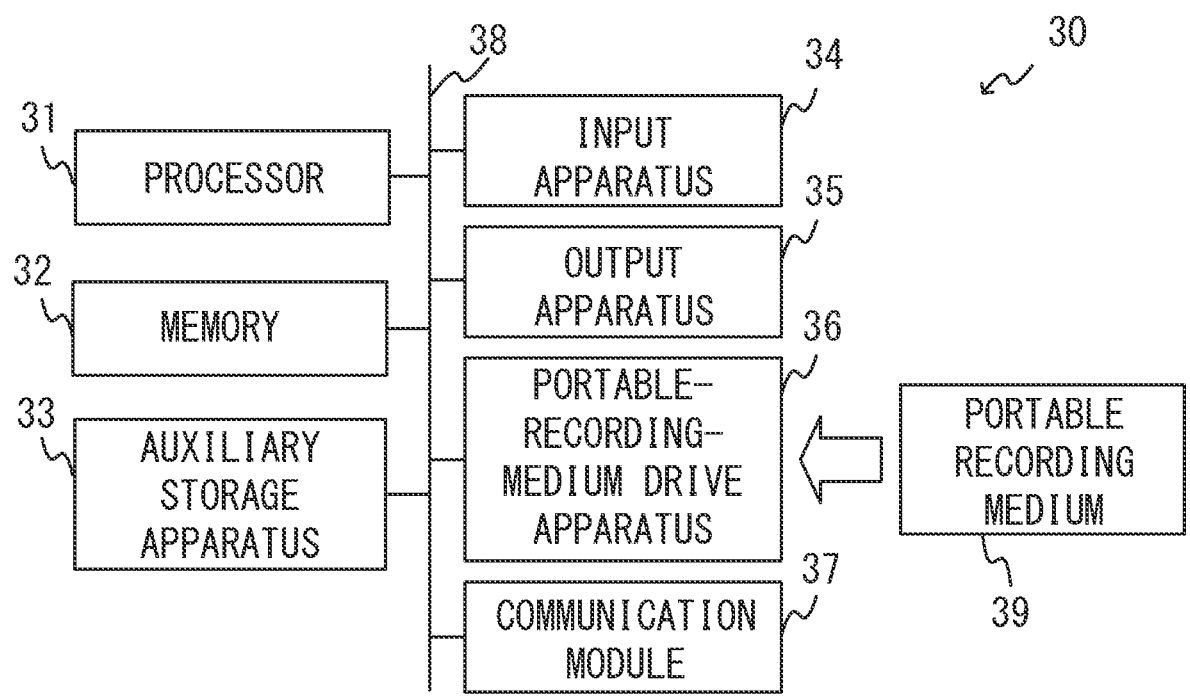
FIG. 4 exemplifies the physical configuration of a control apparatus.

FIG. 2 exemplifies the configuration of a cell culture monitoring system. FIG. 3 exemplifies the configuration of an image capturing apparatus. FIG. 4 exemplifies the physical configuration of a control apparatus. Descriptions are given in the following of the configuration of a system 1 depicted in FIG. 2 by referring to FIGS. 2-4.

The system 1 is a cell culture monitoring system for obtaining images of culture cells and monitoring cell culturing on the basis of the images, while culturing the culture cells in a managed environment within an incubator 20. As depicted in FIG. 2, the system 1 includes an image capturing apparatus 10 placed within the incubator 20, and a control apparatus 30. The system 1 is such that the control apparatus 30 counts the number of cells on the basis of an image obtained by the image capturing apparatus 10 and assists a user in monitoring cell culturing by using the obtained cell count. The control apparatus 30 communicates with the image capturing apparatus 10 and client terminals (client terminals 40 and 50). The system 1 may include the incubator 20 and a client terminal.

As depicted in FIG. 2, a culture container 100 is placed on the image capturing apparatus 10 disposed within the incubator 20. For example, the culture container 100 may be, but is not particularly limited to, a petri dish, a flask, or a microplate. As depicted in FIG. 3, the culture container 100 accommodates a culture medium CM and cells C, i.e., culture cells. For example, the culture medium CM may be, but is not particularly limited to, calf blood serum, and the cells C may be, but is not particularly limited to, cartilage cells.

The image capturing apparatus 10 images the cells C accommodated within the culture container 100 so as to generate an image of the cells C (hereinafter, "cell image"). The image capturing apparatus 10 transmits the generated image to the control apparatus 30. The image capturing apparatus 10 and the control apparatus 30 may communicate with each other wirelessly or by a wired link. For example, the image capturing method may be phase-contrast observation, differential-interference-contrast observation, or oblique illumination observation. As long as an image of each individual cell can be captured, the image capturing method is not particularly limited.

More specifically, as depicted in FIG. 3, the image capturing apparatus 10 includes a housing 11 and a stage 12 on which the culture container 100 is placed. The image capturing apparatus 10 also includes an image capturing unit 13 and a scanning mechanism 16 for moving the image capturing unit 13, both of which are positioned within the housing 11 and below the stage 12. The image capturing unit 13 is provided with an image pickup element 14, light sources 15, and an optical system (not illustrated).

For example, the image pickup element 14 may be a charge-coupled-device (CCD) image sensor, or a complementary-MOS (CMOS) image sensor. The light sources 15 are, for example, light emitting diodes (LEDs) and illuminate the culture container 100 from below the stage 12. The light sources 15 may be placed opposite to each other with the image pickup element 14 therebetween. The light sources 15 may emit white light. Red (R) light, which has a long wavelength, is desirably used to reduce damage to cells. For example, the light sources 15 may each selectively emit light having a wavelength corresponding to red (R), green (G), or blue (B) by switching between the wavelengths corresponding to the three colors of red (R), green (G), and blue (B). In the image capturing apparatus 10, light emitted from a light source 15 passes through the bottom surface of the culture container 100, and a portion of light reflected by the upper surface of the culture container 100 passes through the cells C within the culture container 100. The optical system forms an optical image of the cells C on the image pickup element 14 by using the light that has passed through the cells C within the culture container 100.

For example, the scanning mechanism 16 may include a drive source such as a motor and move the image capturing unit 13 in a direction orthogonal to the optical axis of the optical system (in an XY direction). The scanning mechanism 16 moves the image capturing unit 13 in the XY direction, thereby allowing the image capturing apparatus 10 to change the range of image capturing. The scanning mechanism 16 may also move the image capturing unit 13 in the direction of the optical axis of the optical system (Z direction). The image capturing apparatus 10 may adjust a focus position by using the scanning mechanism 16. Alternatively, the image capturing apparatus 10 may adjust the focus position by moving at least one lens among lenses included in the optical system in the direction of the optical axis.

The control apparatus 30 is a computer that controls the system 1. As depicted in FIG. 4, the control apparatus 30 includes a processor 31, a memory 32, an auxiliary storage apparatus 33, an input apparatus 34, an output apparatus 35, a portable-recoding-medium drive apparatus 36 for driving a portable recording medium 39, a communication module 37, and a bus 38. The auxiliary storage apparatus 33 and the portable recording medium 39 are each an example of a non-transitory computer-readable recording medium storing a program.

For example, the processor 31 may be an electric circuit (circuitry) that includes a central processing unit (CPU) and a graphics processing unit (GPU). The processor 31 performs programmed processing, such as a cell information display method (described hereinafter), by loading a program stored in the auxiliary storage apparatus 33 or the portable recording medium 39 into the memory 32 and then executing the loaded program.

For example, the memory 32 may be any semiconductor memory such as a random access memory (RAM). In program execution, the memory 32 functions as a work memory for storing a program or data stored in the auxiliary storage apparatus 33 or the portable recording medium 39. For example, the auxiliary storage apparatus 33 may be a nonvolatile memory such as a hard disk or a flash memory. The auxiliary storage apparatus 33 is used mainly to store various data and programs.

The portable-recording-medium drive apparatus 36 accommodates the portable recording medium 39. The portable-recording-medium drive apparatus 36 can output data stored in the memory 32 or the auxiliary storage apparatus 33 to the portable recording medium 39 and read a program, data, and the like from the portable recording medium 39.

The portable recording medium 39 may be any recording medium that can be carried. For example, the portable recording medium 39 may include an SD card, a universal serial bus (USB) flash memory, a compact disc (CD), and a digital versatile disc (DVD).

The input apparatus 34 is, for example, a keyboard or a mouse. The output apparatus 35 is, for example, a display apparatus or a printer. For example, the communication module 37 may be a wire communication module that communicates with the image capturing apparatus 10, which is connected via an external port. The communication apparatus 37 may be a wireless communication module. The bus 38 connects the processor 30, the memory 32, the auxiliary storage apparatus 33, and the like to each other in a manner such that data can be communicated therebetween.

The configuration depicted in FIG. 4 is an example of the hardware configuration of the control apparatus 30. The control apparatus 30 is not limited to this configuration. The control apparatus 30 may be a general-purpose or special-purpose apparatus. For example, the control apparatus 30 may include a specifically designed electric circuit, e.g., an application specific integrated circuit (ASIC). The control apparatus 30 may be configured using a field-programmable gate array (FPGA).

The control apparatus 30 transmits an image capturing instruction to the image capturing apparatus 10. The control apparatus 30 receives an image generated by the image capturing apparatus 10 imaging the cells C. In addition, on the basis of the image of the cells C obtained from the image capturing apparatus 10, the control apparatus 30 calculates a cell count by counting the number of cells C included in the image. More specifically, the number of cells C is calculated using two different counting models so as to calculate two cell counts (first and second cell counts). By using the cell counts, the control apparatus 30 provides the user with a screen for assisting in the monitoring of cell culturing. In particular, for example, the control apparatus 30 may display, on a display apparatus constituted by the output apparatus 35, a screen for assisting in the monitoring of the cell culturing.

The client terminal 40 is a notebook computer. The client terminal 50 is a tablet computer. The control apparatus 30 may output screen information to a client terminal (client terminal 40 or 50) at a request therefrom. As long as the client terminals include a display unit, the client terminals may be, for example, a desktop computer or a smartphone.

Figure 5:
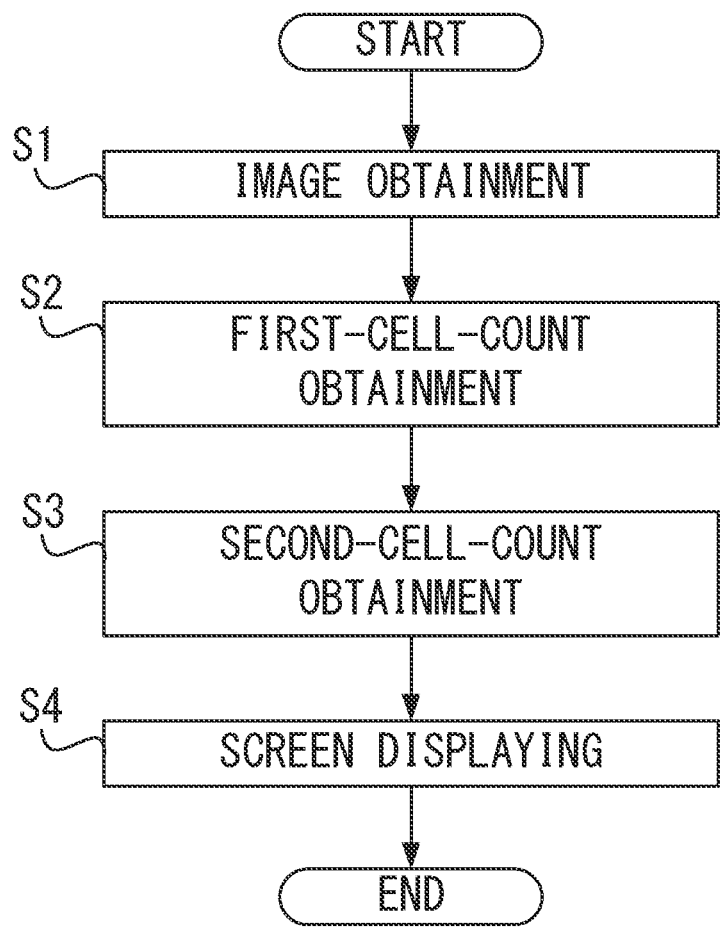
FIG. 5 is a flowchart illustrating an example of a method for assisting in monitoring cell culturing.

FIG. 5 is a flowchart illustrating an example of a method for assisting in monitoring cell culturing. By referring to FIG. 5, the following describes a method implemented by the system 1 for assisting in monitoring cell culturing. The processes depicted in FIG. 5 indicate a method for assisting a user in monitoring cell culturing by displaying cell count information and are thus an example of a cell count information display method. The cell count information includes at least a cell count and may also include information calculated on the basis of the cell count.

As depicted in FIG. 5, the system 1 includes four steps consisting of image obtainment (step S1), first-cell-count obtainment (step S2), second-cell-count obtainment (step S3), and screen displaying (step S4).

In the image obtainment process in step S, the control apparatus 30 obtains cell images generated by the image capturing apparatus 10 imaging cells C. In the system 1, the control apparatus 30 controls the image capturing apparatus 10, which is disposed within the incubator 20 with the culture container 100 placed thereon, so that the control apparatus 30 can obtain cell images without the culture container 100 being taken out of the incubator 20. Thus, the system 1 can obtain cell images while continuing cell culturing. In step S1, the control apparatus 30 obtains a plurality of cell images provided by the image capturing apparatus 10 successively imaging cells.

In the first-cell-count obtainment process in step S2, the control apparatus 30 inputs each of the plurality of cell images obtained in step S1 to a first counting model and obtains a first cell count output from the first counting model. In particular, the control apparatus 30 obtains a first cell count output by applying each of the plurality of cell images to the first counting model. The first cell count is output for each of the cell images. In the second-cell-count obtainment process in step S3, the control apparatus 30 inputs the cell images obtained in step S1 to a second counting model and obtains a second cell count output from the second counting model. In particular, the control apparatus 30 obtains a second cell count output by applying, to the second counting model, each of a plurality of cell images that are the same as the images for which the first cell count has been obtained. The second cell count is output for each of the cell images. The first and second counting models are each a model for counting the number of cells included in an image and different from each other.

The first counting model is typically expected to be used for the above-described monitoring of cell culturing and assesses cells in accordance with a higher standard than the second counting model. In particular, the first counting model has a high precision that serves as an indicator of how accurately target objects have been detected. Meanwhile, the second counting model prioritizes the detection of every target object without fail and assesses cells in accordance with a lower standard than the first counting model. In particular, the second counting model has a high recall factor that serves as an indicator of how comprehensively target objects have been detected. A high resistance to disturbance or the like is attained with a high recall factor, so it can be said that a counting model having a high recall factor has robustness. A precision and a recall factor have a relationship of trade-off, and there is a constraint wherein increasing either of the precision and recall factor of one model causes a decrease in the other.

The first counting model has a higher precision than the second counting model and a lower recall factor than the second counting model. In accordance with the first-cell-count obtainment process in step S2, accordingly, a non-overestimated reliable cell count can be obtained. The second counting model has a higher recall factor than the first counting model and a lower precision than the first counting model. In accordance with the second-cell-count obtainment step in step S3, accordingly, a cell count can be obtained with a stable accuracy during a culture period without excessive response to a change in the shape of cells. Counting models having a high precision, such as the first counting model, is expected to be commonly used because when transplanting cultured cells to a patient or transporting cultured cells to a client, it is essential to satisfy the requirement that as many cells as are equal to or greater than a desired cell count are included, i.e., because the counting based on the first counting model, which counts the number of reliable cells but does not count the number of incorrect objects, is more desirable than the counting based on the second counting model, which is likely to obtain a cell count overestimated in comparison with the actual cell count.

The screen displaying process in step S4 is a process of displaying a screen for assisting in the monitoring of cell culturing on the basis of the first and second cell counts respectively obtained in steps S2 and S3 by the control apparatus 30. More specifically, the control apparatus 30 generates, on the basis of the first and second cell counts, a cell count information display screen on which at least either of the first and second cell counts and a correlation between the first and second cell counts are visualized, and displays the generated cell count information display screen on the display apparatus. More desirably, the control apparatus 30 generates, on the basis of a first-cell-count history and a second-cell-count history, a cell count information display screen on which a change in at least either of the first and second cell counts with respect to time and a change in a correlation between the first and second cell counts with respect to time are visualized, and displays the generated cell count information display screen on the display apparatus.

The system 1 displays at least either of the first and second cell counts on the screen, so the user can perform culture monitoring based on the cell count. In addition, the correlation between the first and second cell counts is displayed on the screen, so that when a cell count or a temporal variation therein is different from an expected value, it can be distinguished, without checking an image, whether a culture environment is the cause or whether a fault in image recognition is the cause.

More specifically, when the cell counts provided by the first counting model prioritizing precision and the second counting model prioritizing recall factor deviate, with similar tendencies, from an expected temporal variation, it can be determined that a change that does not conform to the expected temporal variation is likely to have actually occurred in the cell count and that the temporal variation is unlikely to result from a fault in image recognition. When the first and second counting models each exhibit a different tendency of temporal variation in cell count, especially when the first counting model has a deviation from an expected temporal variation, it can be determined that the deviation is likely to result from a fault in image recognition. Accordingly, the system 1 can decrease opportunities to check an image in detail so as to distinguish a cause, thereby reducing the task burden on the user.

The following describes a specific example of a method implemented by the system 1 for assisting in monitoring cell culturing.

First Embodiment

Figure 6:
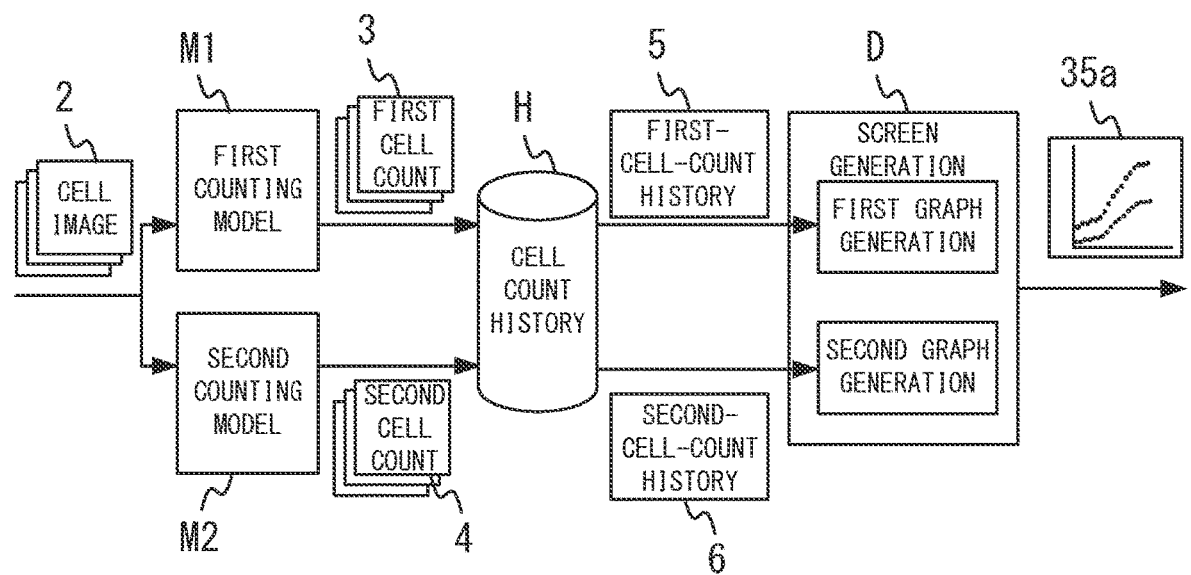
FIG. 6 is an explanatory diagram for an example of a flow of processes up to generation of a cell count information display screen.
Figure 7:
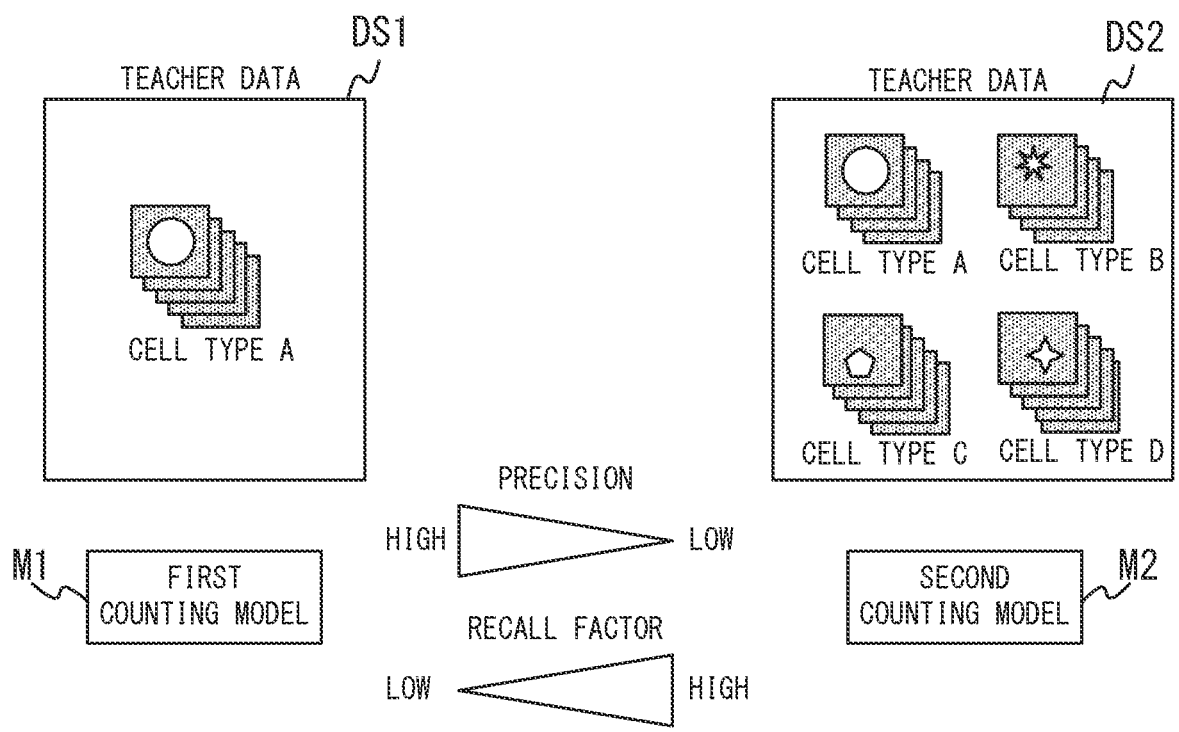
FIG. 7 is an explanatory diagram for a first counting model and a second counting model.
Figure 8:
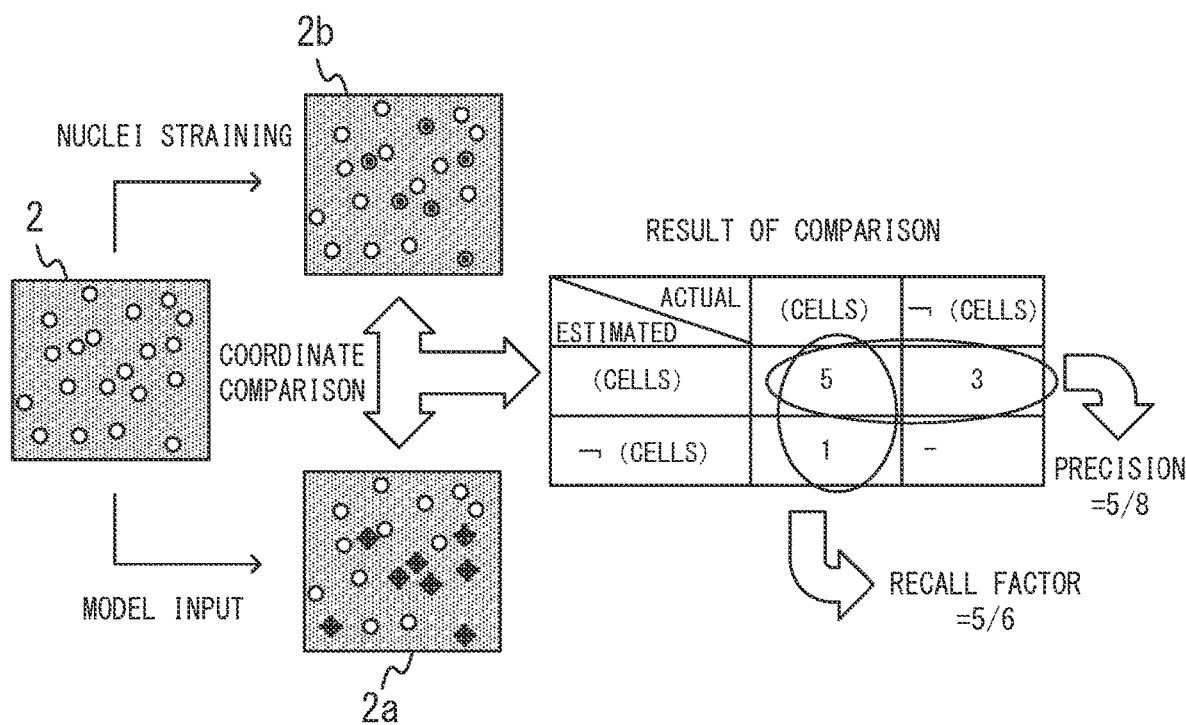
FIG. 8 is an explanatory diagram for a method for verifying the precision and the recall factor of a counting model.
Figure 9:
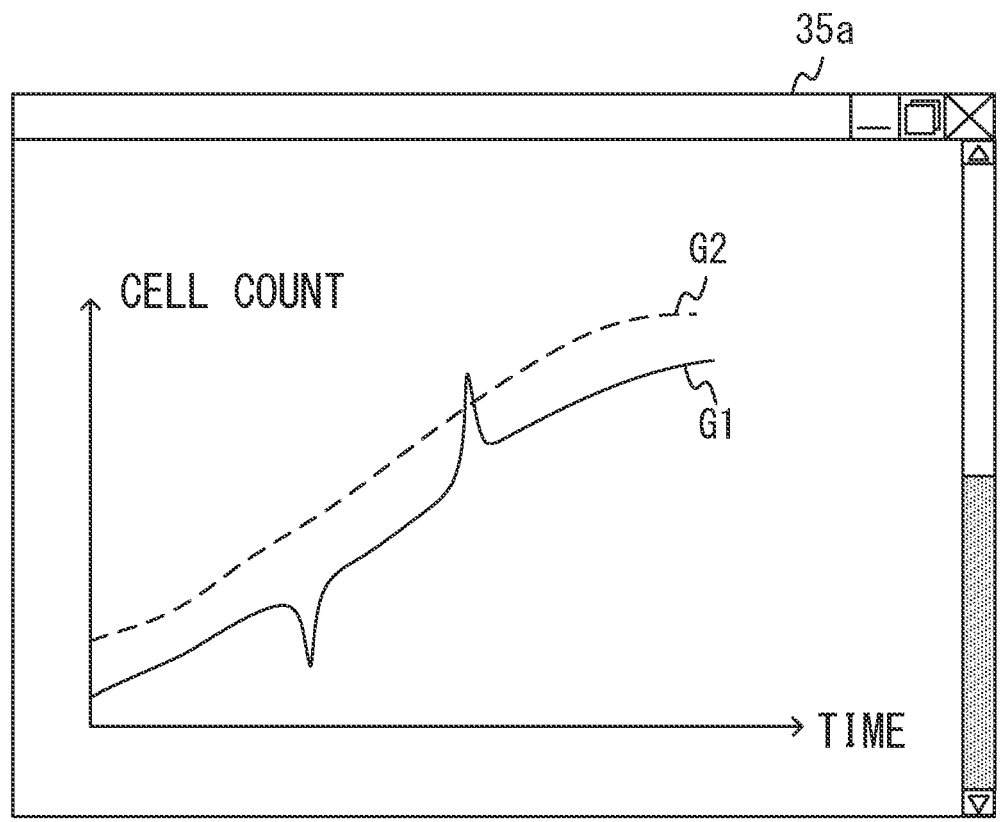
FIG. 9 illustrates an example of a cell count information display screen.

FIG. 6 is an explanatory diagram for an example of a flow of processes up to generation of a cell count information display screen. FIG. 7 is an explanatory diagram for a first counting model and a second counting model. FIG. 8 is an explanatory diagram for a method for verifying the precision and the recall factor of a counting model. FIG. 9 illustrates an example of a cell count information display screen. FIG. is an explanatory diagram for how to distinguish an abnormality cause on the basis of on a cell count information display screen. By referring to FIGS. 6-10, the following describes a monitoring assisting method in accordance with the first embodiment implemented by the system 1 by taking examples in which cartilage cells are cultured. In the system 1, a cell count information display screen is displayed to provide user assistance in cell culturing, so the method implemented by the system 1 so as to display cell count information is a method for assisting in monitoring cell culturing.

In the system 1, as indicated in FIG. 6, the control apparatus 30 inputs a cell image 2 of cartilage cells generated by the image capturing apparatus 10 to a first counting model M1 and a second counting model M2, and stores, in a history unit H, a first cell count 3 output from the first counting model M1 and a second cell count 4 output from the second counting model M2. The cell image 2 is an image of culture cells within the culture container 100 disposed in the incubator 20. Such a process is performed every time a cell image 2 is input, and accordingly a first-cell-count-3 history 5 and a second-cell-count-4 history 6 are accumulated in the history unit H. The first-cell-count-3 history 5 includes a plurality of first cell counts 3 corresponding to a plurality of cell images 2. The second-cell-count-4 history 6 includes a plurality of second cell counts 4 corresponding to a plurality of cell images 2.

The first counting model M1 is a machine learning model using a neural network, which may be, for example, a trained machine learning model that has been trained using, as teacher data DS1, images of a cell type A that is the same as the type of cells included in a cell image (the type of cartilage cells with reference to this example). By contrast, the second counting model M2 is a machine learning model using a neural network, which may be, for example, a trained machine learning model that has been trained using, as teacher data DS2, images of the cell type A that is the same as the type of cells included in the cell image (the type of cartilage cells with reference to this example) and images of cell types (cell types B, C, and D) that are different from the type of cells included in the cell image (the type of cartilage cells with reference to this example).

The first counting model M1, which has learned only cells of the same type as the cartilage cells, can recognize the cartilage cells in accordance with a stricter standard than the second counting model M2, which has learned the cartilage cells and other cells. Thus, the first counting model M1 has a higher precision for cartilage cells than the second counting model M2. The second counting model M2, which has learned cells of various types or cells with various shapes, has a decreased precision for counting the number of cartilage cells in comparison with the first counting model M1, but can more comprehensively recognize all the cells in an image than the first counting model M1. Thus, the second counting model M2 has a higher recall factor for cartilage cells than the first counting model M1.

For example, the precision and the recall factor of each model can be checked using a method such as that depicted in FIG. 8. First, a cell image 2 is input to a model for which a precision and a recall factor are to be checked, and an output image 2a including coordinate information of detected cartilage cells is obtained. Second, the nuclei of the cartilage cells are stained, and then the cartilage cells are imaged to obtain a staining image 2b. Third, coordinate information of the cells having the stained nuclei is obtained from the staining image 2b, and the obtained coordinate information is compared with the coordinate information included in the output image 2a. Fourth, the precision and the recall factor of the model are calculated from a result of the comparison.

The precision is calculated according to the ratio between the number of objects recognized as cartilage cells by the model (eight objects with reference to this example) and the number of objects actually confirmed as cartilage cells according to the staining image 2b among the objects recognized as cartilage cells by the model (five objects with reference to this example) (the ratio is 5/8 with reference to this example). The recall factor is calculated according to the ratio between the number of objects actually confirmed as cartilage cells according to the staining image 2b (six objects with reference to this example) and the number of objects recognized as cartilage cells by the model among the objects actually confirmed as cartilage cells according to the staining image 2b (five objects with reference to this example) (the ratio is 5/6 with reference to this example).

When cell counts are accumulated in the history unit H, the control apparatus 30 reads the first-cell-count history 5 and the second-cell-count history 6 accumulated in the history unit H, and inputs the same to a screen generation unit D. Then, the control apparatus 30 displays, on the output apparatus 35, a screen 35a, i.e., a cell count information display screen generated by the screen generation unit D.

More specifically, the screen generation unit D performs a first graph generation process for generating a first graph G1 indicating a change in the first cell count with respect to time on the basis of the first-cell-count history 5, and a second graph generation process for generating a second graph G2 indicating a change in the second cell count with respect to time on the basis of the second-cell-count history 6. Accordingly, as depicted in FIG. 9, the screen 35a displayed on the output apparatus 35 includes the first graph G1 and the second graph G2. That is, when displaying the screen 35a, the control apparatus 30 displays the first graph G1 and the second graph G2 on the output apparatus 35.

Displaying the first graph G1 and the second graph G2 visualizes a change in the correlation between the first and second cell counts with respect to time by means of the relationship between the first graph G1 and the second graph G2. Thus, by checking the screen 35a, a user who understands an appropriate temporal variation in a cell count can check whether the cell count has been exhibiting a normal temporal variation, and can distinguish whether a culture environment is a cause of an abnormality or whether a fault in image recognition is the cause of the abnormality.

Figure 10:
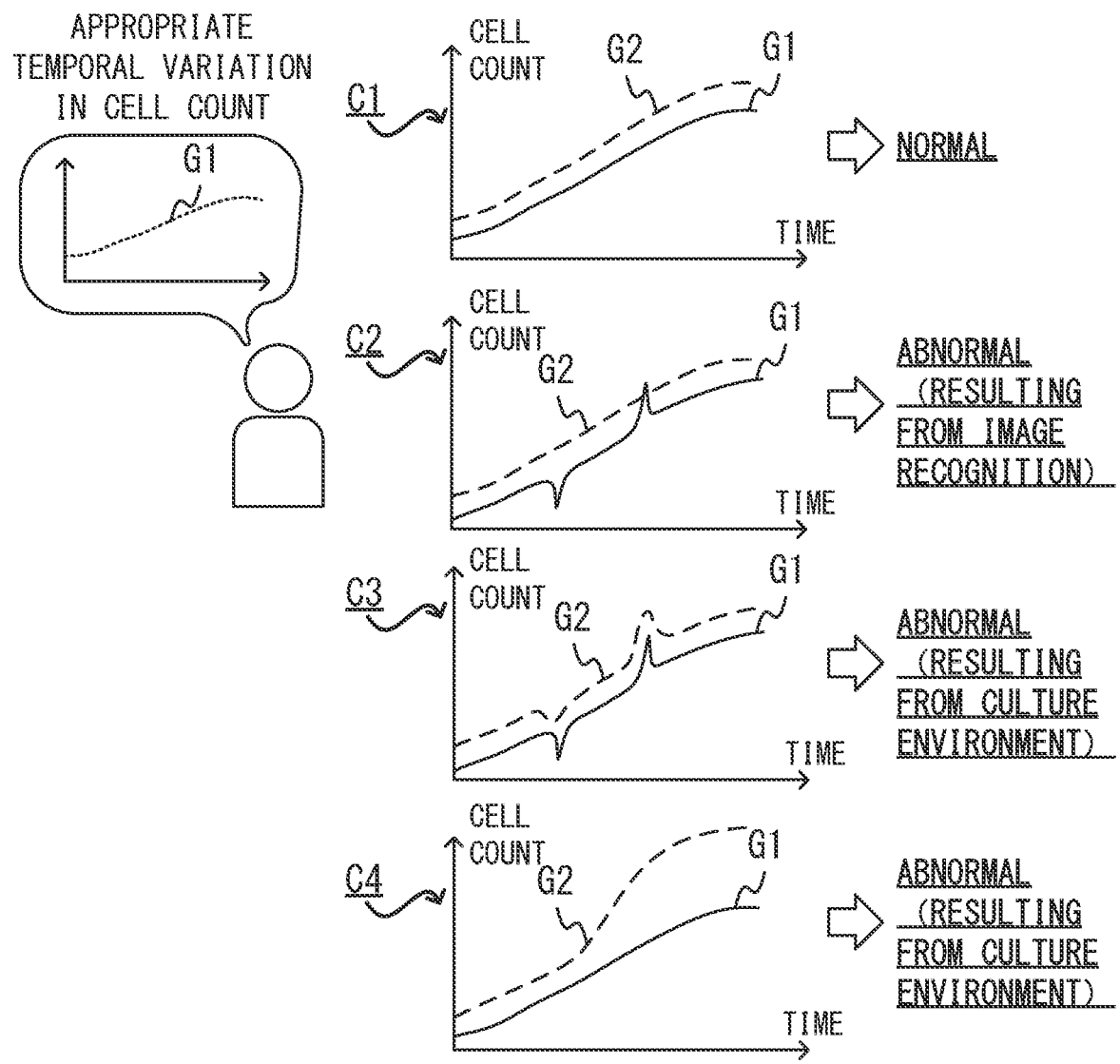
FIG. 10 is an explanatory diagram for how to distinguish an abnormality cause on the basis of a cell count information display screen.

In particular, when, as indicated by a case C1 in FIG. 10, the first graph G1 and the second graph G2 do not indicate a remarkably different trend from an appropriate temporal variation in the cell count, and exhibit temporal variations while maintaining a constant relationship therebetween, the user can determine that cell culturing has been performed normally.

By contrast, when, as indicated by cases C2-C4 in FIG. 10, the first graph G1 and the second graph G2 exhibit temporal variations without maintaining a constant relationship therebetween or at least either the first graph G1 or the second graph G2 indicates a remarkably different trend from the appropriate temporal variation in the cell count, the user may determine that there could be an abnormality.

More specifically, when only the first graph G1 exhibits an unnatural change as indicated in the case C2 in FIG. 10, it may be considered that, due to a change in the shape of the cells, the cell count have not been correctly obtained using the first counting model which accesses the cells in accordance with the stricter standard. For example, when multi-layering of cells has occurred, the second graph G2 does not exhibit a remarkable change, because the second counting model can recognize the cells after the shape change caused by the multi-layering. By contrast, the first counting model could become, as soon as a standard shape is lost, incapable of recognizing cells and thus exhibit a variation in the obtained cell count, despite no change in the actual cell count. Thus, it can be determined that a fault in image recognition is likely to have occurred, rather than an abnormality in the culture environment.

It can be determined whether an unnatural change has occurred by focusing attention on a change in the first graph G1 alone or the relationship between the first graph G1 and the second graph G2. For example, it may be determined that an unnatural change has occurred when the first graph G1 and the second graph G2 are largely spaced apart from each other or when the magnitude relationship between the second cell count and the first cell count is reversed.

When, as indicated by the case C3 in FIG. 10, the first graph G1 and the second graph G2 both exhibit an unnatural change, it may be determined that there is actually an unnatural change in the cell count. In particular, it may be determined that an abnormality resulting from the culture environment or from variations between the cells in quality is likely to have occurred.

In addition, when, as indicated by the case C4 in FIG. 10, the relationship between the first graph G1 and the second graph G2 starts to clearly change in the middle of cell culturing, it may be determined that an abnormality resulting from the culture environment is likely to have occurred. Especially when, as indicated by the case C4 in FIG. 10, the cell count indicated by the graph G2 starts to significantly increase in the middle of cell culturing, it may be considered that intrusion of dirt or the like could possibly have occurred. Assuming that the user was performing a manipulation such as the replacing of the medium or the opening or closing of the incubator at the time at which a clear change in the relationship between the first graph G1 and the second graph G2 occurred, it may be determined that contamination has occurred due to the manipulation, and the user can think back about what culturing operation was performed at that time. In addition, when the cell count indicated by the graph G2 increases and the cell count indicated by the graph G1 decreases, it may be considered that there could be a change in the cartilage cells for which counting is performed. In particular, it may be inferred that a shape change associated with death, canceration, or aging of the cartilage cells (i.e., a decrease in the number of target cells) is likely to have occurred.

As described above, by using the cell count information display method in accordance with the present embodiment, the system 1 can assist the user in distinguishing, without checking an image, a cause of an abnormality in a cell count obtained from the image. Thus, the task burden on the user can be significantly reduced. Moreover, when the first graph G1 and the second graph G2 each change with a different trend, even a user who does not understand an appropriate temporal variation in the cell count can easily determine that an abnormality could possibly have occurred.

Figure 11:
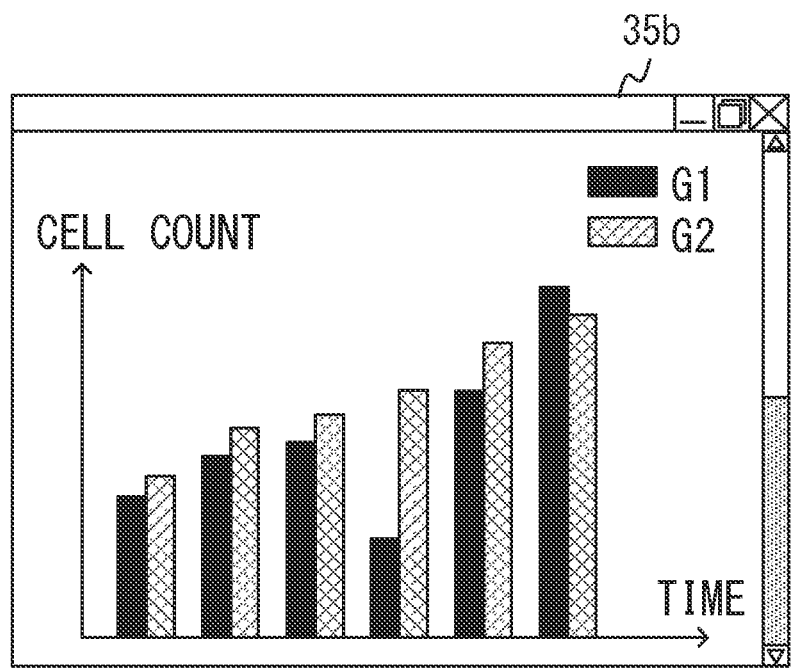
FIG. 11 illustrates another example of a cell count information display screen.

FIG. 11 illustrates another example of the cell count information display screen. FIG. 9 depicts an example in which the first graph G1 and the second graph G2 are sequential line graphs, but other types of graphs may be used. For example, as indicated by a screen 35b in FIG. 11, the system 1 may display changes in the first cell count with respect to time (first graph) and changes in the second cell count with respect to time (second graph) by using bar graphs.

Figure 12:
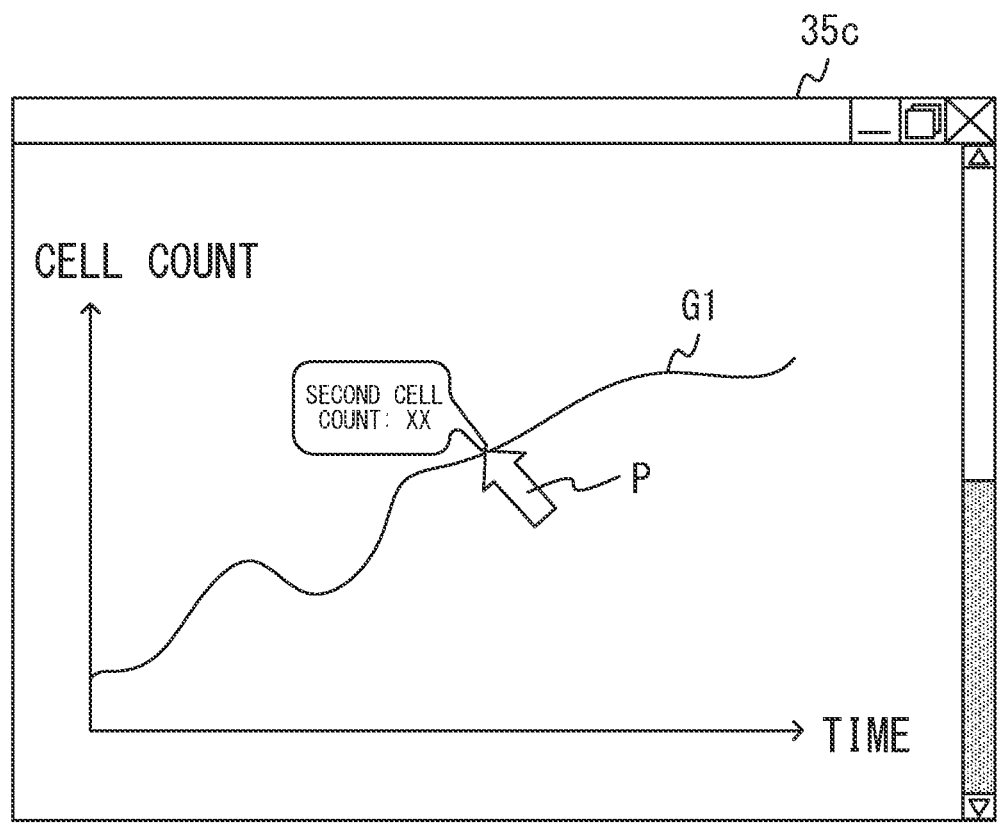
FIG. 12 illustrates still another example of a cell count information display screen.

FIG. 12 illustrates a still further example of the cell count information display screen. While FIGS. 9 and 11 depict examples in which both the first graph G1 and the second graph G2 are displayed, the cell count information display screen may display at least either of these graphs so that a change in the cell count can be easily checked. For example, the system 1 may display only the first graph G1 as seen in a screen 35c depicted in FIG. 12, and the user may place a pointer on the first graph G1 such that the second cell count may be displayed for a time corresponding to the position of the pointer P. In this case, the second cell count is displayed, so the correlation between the first and second cell counts is visualized on the screen 35c. Hence, a cause of an abnormality in the cell count can also be distinguished without checking an image.

Figure 13:
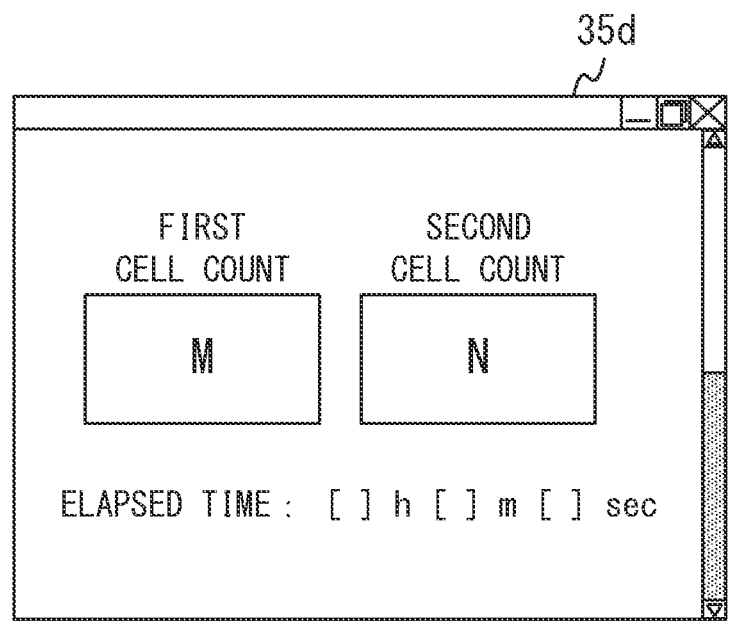
FIG. 13 illustrates yet another example of a cell count information display screen.

FIG. 13 illustrates yet another example of the cell count information display screen. While FIGS. 9 and 11 depict examples in which graphs indicating a change in the cell count with respect to time are displayed, the cell count information display screen may directly display the cell count. For example, as indicated by a screen 35d in FIG. 13, the system 1 may display the values of the first and second cell counts next to each other. In this case, the displayed first and second cell counts are updated as necessary, thereby allowing the user to understand the correlation between the first and second cell counts and a temporal change therein. Hence, as in the other display examples, a cause of an abnormality in the cell count can be distinguished without checking an image.

Second Embodiment

Figure 14:
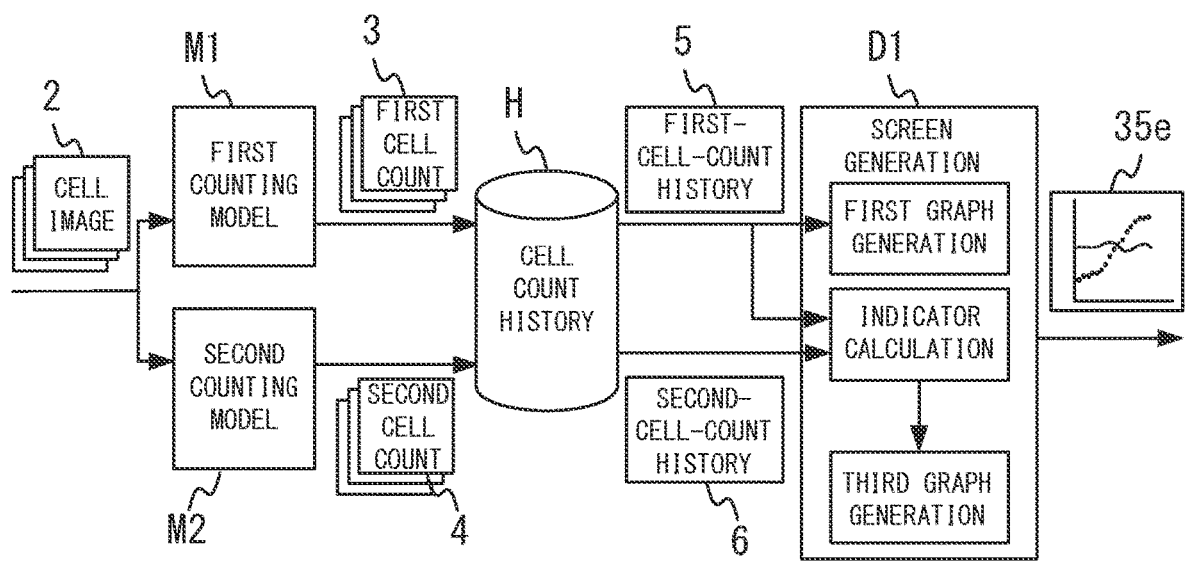
FIG. 14 is an explanatory diagram for another example of a flow of processes up to generation of a cell count information display screen.
Figure 15:
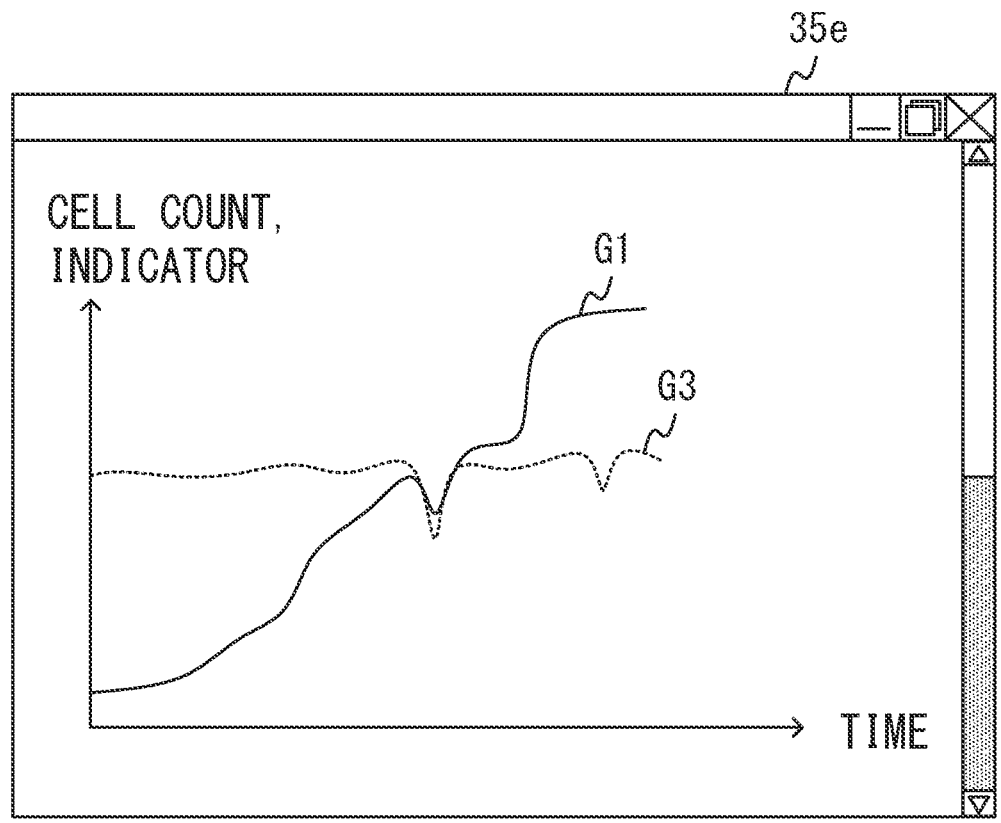
FIG. 15 illustrates a further example of a cell count information display screen.
Figure 16:
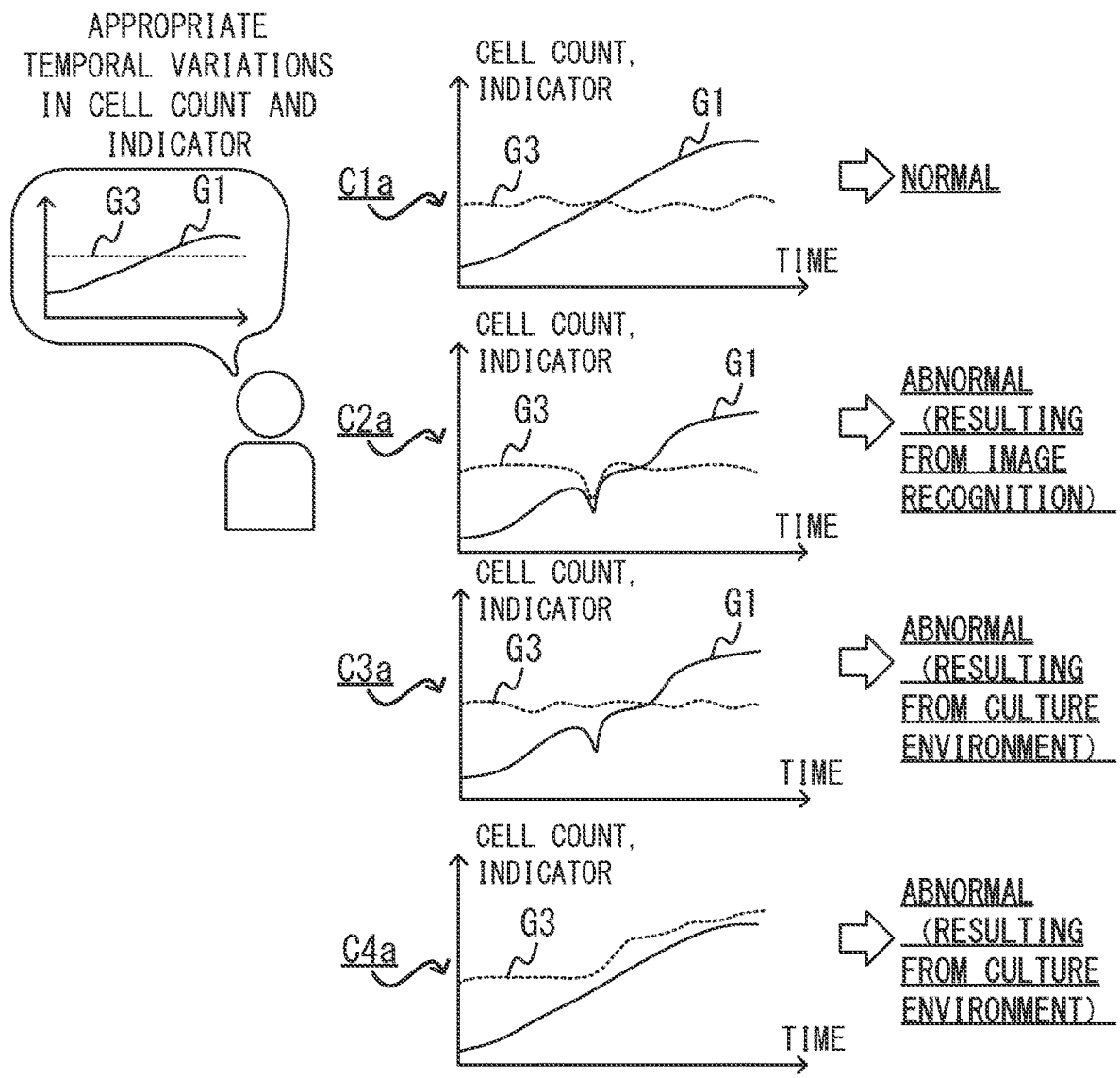
FIG. 16 is an explanatory diagram for how to distinguish an abnormality cause on the basis of a cell count information display screen.

FIG. 14 is an explanatory diagram for another example of a flow of processes up to generation of the cell count information display screen. FIG. 15 illustrates a further example of the cell count information display screen. FIG. 16 is an explanatory diagram for how to distinguish an abnormality cause on the basis of the cell count information display screen. By referring to FIGS. 14-16, the following describes a monitoring assisting method in accordance with the second embodiment implemented by the system 1 with reference to examples in which cartilage cells are cultured. The present embodiment is different from the first embodiment in that in the present embodiment, an indicator of a difference in result of cell recognition between the first and second counting models is visualized. The indicator may one indicating a difference in a result of cell recognition that is calculated on the basis of the first and second cell counts, e.g., the ratio between the first and second cell counts, the difference between the first and the second cell counts, the square of the difference.

In the system 1, as indicated in FIG. 14, the control apparatus 30 inputs a cell image 2 of cartilage cells to the first counting model M1 and the second counting model M2, and stores, in the history unit H, a first cell count 3 output from the first counting model M1 and a second cell count 4 output from the second counting model M2. In addition, the control apparatus 30 reads a first-cell-count-3 history 5 and a second-cell-count-4 history accumulated in the history unit H, and inputs the same to a screen generation unit D1.

The screen generation unit D1 performs a first graph generation process for generating a first graph G1 indicating a change in the first cell count with respect to time on the basis of the first-cell-count history 5, an indicator calculation process for calculating the indicator for each individual time on the basis of the first-cell-count history 5 and the second-cell-count history 6, and a third graph generation process for generating a third graph G3 indicating a change in the indicator with respect to time. Accordingly, as depicted in FIG. 15, a screen 35a displayed on the output apparatus 35 includes the first graph G1 and the third graph G3. That is, when displaying the screen 35e, the control apparatus 30 displays the first graph G1 and the third graph G3 on the output apparatus 35.

Displaying the first graph G1 and the third graph G3 visualizes a change in the correlation between the first and second cell counts with respect to time by means of the relationship between the first graph G1 and the third graph G3. Thus, by checking the screen 35e, a user who understands an appropriate temporal variation in the cell count can check whether the cell count has been exhibiting a normal temporal variation, and can distinguish whether a culture environment is a cause of an abnormality or whether a fault in image recognition is the cause.

In particular, when, as indicated by a case C1a in FIG. 16, the first graph G1 does not indicate a remarkably different trend from an appropriate temporal variation in the cell count and the third graph G3 exhibits a temporal variation with a constant trend, e.g., falls within a certain range, the user can determine that cell culturing has been performed normally.

By contrast, when, as indicated by cases C2a-C4a in FIG. 16, the third graph G3 does not exhibit a temporal variation with a constant trend or the first graph G1 indicates a remarkably different trend from the appropriate temporal variation in the cell count, the user may determine that there could be an abnormality.

More specifically, when, as indicated by the case C2a in FIG. 16, the first graph G1 exhibits an unnatural change and the third graph G3 varies in accordance with the unnatural change, it may be considered that due to a change in the shape of the cells, the cell count may not have been correctly obtained using the first counting model which assesses the cells in accordance with a stricter standard. Thus, it can be determined that a fault in image recognition is likely to have occurred, rather than an abnormality in the culture environment. This is because it can be determined according to the relationship between the first graph G1 and the third graph G3 that there is no unnatural change in the second cell count, so that a determination similar to that for the case C2 depicted in FIG. 10 can be made.

When, as indicated by the case C3a in FIG. 16, the first graph G1 exhibits an unnatural change but the third graph G3 does not vary in accordance with the unnatural change, it may be determined that there is actually an unnatural change in the cell count. In particular, it may be determined that an abnormality resulting from the culture environment is likely to have occurred. This is because it can be determined according to the relationship between the first graph G1 and the third graph G3 that an unnatural change similar to that in the first cell count has occurred in the second cell count, so that a determination similar to that for the case C3 depicted in FIG. 10 can be made.

In addition, when, as indicated by the case C4a in FIG. 16, the trend of the third graph G3 starts to exhibit a clear change in the middle of cell culturing, it may be determined that an abnormality resulting from the culture environment is likely to have occurred. This is because it can be determined according to the relationship between the first graph G1 and the third graph G3 that an unnatural change has occurred only in the second cell count, so that a determination similar to that for the case C4 depicted in FIG. 10 can be made.

As described above, by using the cell count information display method in accordance with the present embodiment, the system 1 can attain effects similar to those attained when the cell count information display method in accordance with the first embodiment is used.

Figure 17:
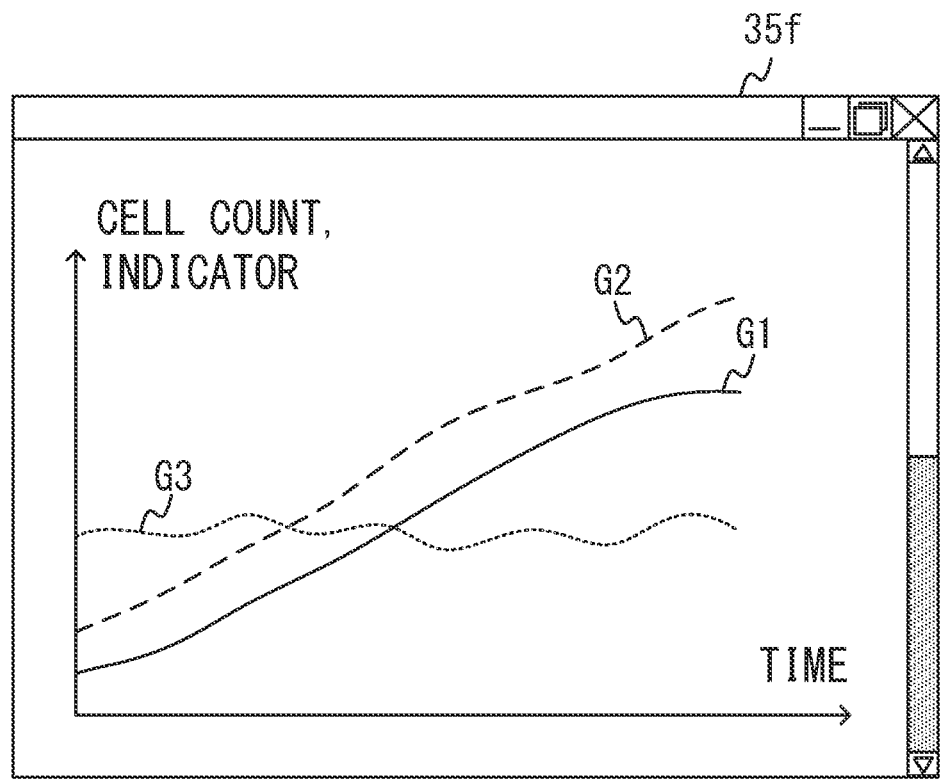
FIG. 17 illustrates a still further example of a cell count information display screen.

FIG. 17 illustrates a still further example of the cell count information display screen. While FIG. 15 indicates an example in which the first graph G1 and the third graph G3 are displayed, the system 1 may display, for example, the first graph G1, the second graph G2, and the third graph G3, as in a screen 35f depicted in FIG. 17. The system 1 may display the third graph G3 and at least either the first graph G1 or the second graph G2, and thus may display the second graph G2 and the third graph G3 without displaying the first graph G1.

The embodiments described above indicate specific examples to facilitate understanding of the invention, and the present invention is not limited to these embodiments. Some of the embodiments described above may be applied to other embodiments. Various modifications or changes can be made to the method for displaying cell count information, the system, and the computer-readable medium without departing from the recitation in the claims.

Figure 18:
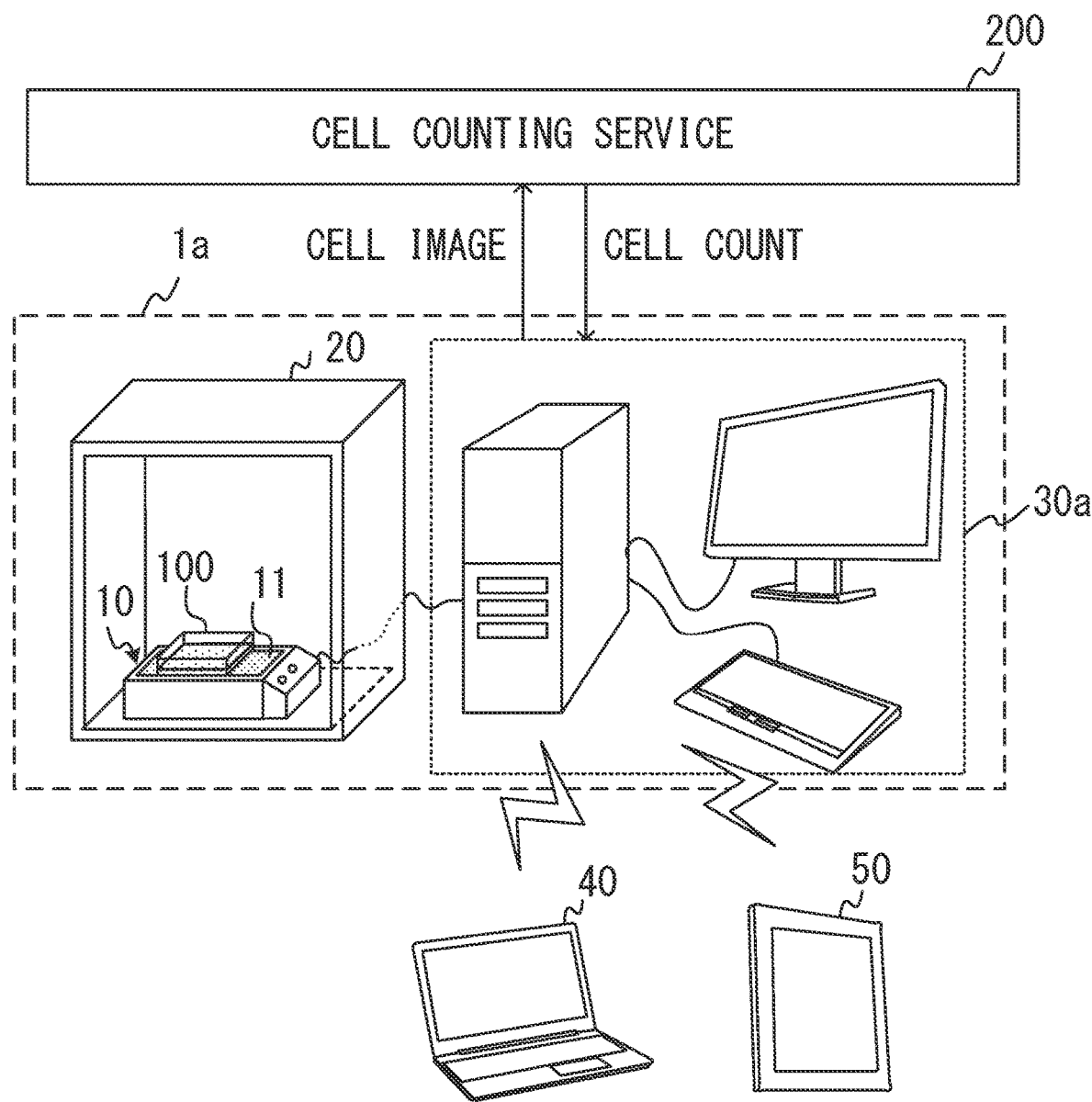
FIG. 18 illustrates a variation of the configuration of a cell culture monitoring system.

In the examples indicated for the embodiments described above, the number of cells is counted within the system 1. However, the number of cells may be counted outside the system 1. For example, as indicated by a system 1a depicted in FIG. 18, the first and second cell counts may be obtained using an external service for counting the number of cells (cell counting service 200). A control apparatus 30a of the system 1a is similar to the control apparatus 30 expect that the control apparatus 30a obtains a cell count from the cell counting service 200 external to the system 1a.

In the examples indicated for the embodiments described above, two counting models are used. However, at least two counting models may be used, or three or more counting models may be used to obtain a cell count. As long as the difference in characteristic between counting models is known in advance, a cause of an abnormality can be inferred from the relationship between cell counts output from the counting models, and the cause can be distinguished without checking an image.

In the examples indicated above for the embodiments described above, the cell count information display screen is displayed. In one possible example, the user may select a particular position within the cell count information display screen, such that a cell image obtained at a time corresponding to the selected position is displayed in, for example, a pop-up manner. In this way, owing to the cell count information display screen, a situation for which an image needs to be actually checked can be specified, with a cause of an abnormality being distinguished, and the image can be checked through a simple operation. Hence, the task burden on the user can be further reduced owing to a decrease in the number of times the image is checked and the simplification of the image checking task.

When the counting models are machine learning models, the user may check, within an image displayed on the cell count information display screen, a fault in image recognition, and then only the first counting model or both of the first and second counting models may be trained using the image as teacher data. Accordingly, the precision of the first counting model can be improved, thereby improving the reliability of the first cell count used by the user to determine whether the culture cells have reached a target number, while maintaining the relationship between the first and second counting models.

The above embodiments have been described by taking the examples in which the counting models are trained machine learning models using a neural network. However, the counting models are not limited to ones using a neural network and may be other machine learning models. A model other than a machine learning model may be used, and a model that counts the number of cells on the basis of a particular rule may be used. For example, a counting model that counts the number of cells by using template matching may be used, or a counting model that counts the number of cells from a binarized image may be used. A counting model that counts the number of cells by counting the number of stained nuclei may be used. As long as the combination of a counting model prioritizing precision and a counting model prioritizing recall factor is used, the combination of a machine learning model and a rule-based counting model may be used. A counting model that counts the number of cells from a binarized image may be used as the counting model prioritizing recall factor, and a counting model that counts the number of stained nuclei may be used as the counting model prioritizing precision.

In the examples indicated for the embodiments described above, the number of cells is counted. However, the number of colonies may be counted in addition to the number of cells. Since colonies are sets of cells, recognizing cells and obtaining the positional relationship between the cells allows colonies to be identified. Counting the number of colonies in addition to the number of cells allows the user to be provided with more information pertaining to cell culturing.

In the examples indicated for the embodiments described above, the user detects an abnormality. However, the system 1 may detect an abnormality and report the detected abnormality to the user by displaying the same on the screen. For example, when the difference between the first and second cell counts is equal to or greater than a certain value or is equal to or less than another certain value, this fact may be reported to the user. At the same time, for example, the system 1 may display the screen 35a depicted in FIG. 9. A user who checked the screen 35a according to the report can distinguish the abnormality cause on the basis of the information on the screen 35a. Alternatively, the control apparatus 30 may specify and report the cause of an abnormality to the user.

The report may be transmitted through wireless communication by, for example, a smartphone or a tablet computer, i.e., a portable terminal owned by a user. For example, the wireless communication may be performed using WiFi, LTE, NFC, or Bluetooth®. The report may be sent via any network such as PAN, LAN, or WAN. Accordingly, the user can find out whether there is an abnormality in culture cells even without staying in the vicinity of the incubator or staying in the operation room. When the control apparatus 30 can determine whether an abnormality has occurred, even an inexperienced operator who can hardly determine whether there is an abnormality by viewing a cell count or even an operator who cannot intuitively determine whether there is an abnormality can easily find out that an abnormality has occurred. The report may be displayed on the screen of a computer or the like installed in the vicinity of the incubator or in the operation room. The report may be displayed on a screen similar to the screen 35a on which the graph depicted in FIG. 9 is displayed.

Figure 19:
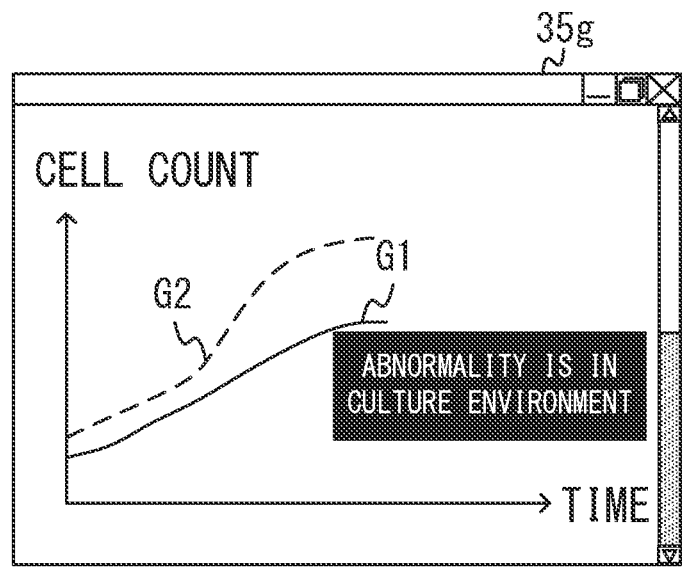
FIG. 19 illustrates a yet further example of a cell count information display screen.

In the examples indicated for the embodiments described above, a use who checked the screen display distinguishes the cause of an abnormality. However, the control apparatus 30 may decide the abnormality cause on the basis of information used for the screen display and report the decided cause to the user. For example, in a case where the screen 35a depicted in FIG. 9 is displayed, when detecting that the first cell count has surpassed the second cell count or that the first cell count has become less than the second cell count by a certain degree or greater, the control apparatus 30 may decide that a fault in image recognition is the cause of an abnormality, and report this fact to the user. The cause of the abnormality specified through the decision may be displayed in an overlaid manner on a screen displaying the graph. Meanwhile, when detecting that the difference between the first and second cell counts that had been kept constant in some degree has started to remarkably change, the control apparatus 30 may decide that an abnormality has occurred in the culture environment, and report this fact to the user. As indicated in FIG. 19, the cause of the abnormality specified through the decision may be displayed in an overlaid manner on a screen 35g displaying the graph. In FIG. 9, the control apparatus 30 may display the occurrence of the abnormality and the cause thereof in an overlaid manner on the graph at an image capturing time for which it has been decided that the abnormality occurred thereat. For example, the possibility of occurrence of an abnormality may be displayed using a rate. The possibility of occurrence of an abnormality may be estimated from, for example, the amount of change in the relationship between the first and second cell counts. For example, the abnormality cause decided by the control apparatus 30 may be an abnormality in the cell culture environment, an abnormality in image recognition, or the combination of an abnormality in the culture environment and an abnormality in image recognition. The user may distinguish the abnormality cause by reference to the screen display and a decision result provided by the control apparatus 30 (abnormality cause). When the occurrence of an abnormality and the cause thereof are displayed on the graph in an overlaid manner, the user can avoid, by seeing the graph, troubles with inferring the abnormality cause, and in addition, even an inexperienced operator who can hardly determine the cause of the abnormality by viewing a cell count and even an operator who cannot intuitively determine that there is an abnormality can specify the cause of the abnormality owing to the assistance in specifying the abnormality cause.

The embodiments described above are based on the assumption that the environment of cell culturing is monitored in real time. However, a set of cell images successively captured during a culture period may be used such that the quality of the culturing can be checked to review the culturing. For example, the user can calculate the first and second cell counts by applying the first and second counting models to a plurality of cell images serving as a result of past culturing, and review whether an abnormality occurred in the culture environment at a particular image-capturing time point or whether an image was incorrectly recognized at a particular image-capturing time point. Clarifying the image capturing time at which an abnormality occurred in the culture environment allows for review of a manipulation performed by the operator at that time and the culture environment thereat. Clarifying whether an image was incorrectly recognized allows for improvement of the counting models. In the reviewing, the abnormality cause may be decided by the user with a graph or the like displayed, or may be decided using the control apparatus 30 or an external cell counting service.

In the examples indicated for the embodiments described above, a temporal variation in a cell count is displayed. A temporal variation in a cell count may be displayed according to need. For example, the system 1 may omit the screen display process in step S4 depicted in FIG. 5 and, instead of this process, perform the process of reporting an abnormality occurrence to the user upon detecting an abnormality in the culture environment on the basis of the relationship between the first and second cell counts. The user, upon receipt of the report, may check culture cells so as to check details of the abnormality.

With reference to the above embodiments, the difference between the counting models have been described using the concept of precision and the concept of recall factor. However, a counting model having a high specificity may be used instead of the second counting model, which has a high recall factor, and compared with the first counting model, which has a high precision. The specificity is an indicator of a negative accuracy indicating how accurately a negativity decision as to whether an object to be observed is a non-target object was performed. Thus, a counting model having a high specificity reliably detects objects other than target cells (e.g., dirt, non-target cells, dead cells), i.e., serves for, so to speak, noise decision, rather than functioning for counting the number of cells.

Although the terms "precision," "recall factor," and "specificity" are used herein, these are not the only appropriate words, as long as similar meanings can be expressed. In particular, a "degree of accuracy" and a "positive predictive value (PPV)" can be terms used to mean precision, a "sensitivity" and a "true positive rate" can be terms used to mean recall factor, and a "true negative rate" can be a term used to mean specificity.

What is claimed is:

1. A method for displaying cell count information, the method comprising:
   obtaining a plurality of cell images generated by successively imaging cells;
   obtaining a first cell count output by applying each of the plurality of cell images to a first counting model, the first counting model being for counting a number of cells included in an image;
   obtaining a second cell count output by applying, to a second counting model, each of a plurality of cell images that are the same as the images for which the first cell count has been obtained, the second counting model being for counting a number of cells included in an image, and being different from the first counting model; and
   displaying, on the basis of the first and second cell counts, a screen on which at least either of the first and second cell counts and a correlation between the first and second cell counts are visualized;
   wherein the first counting model has a higher precision than the second counting model and a lower recall factor than the second counting model;
   the displaying the screen comprises displaying the screen on the basis of a first-cell-count history including a plurality of first cell counts corresponding to the plurality of cell images and a second-cell-count history including a plurality of second cell counts corresponding to the plurality of cell images, and
   a change in at least either of the first and second cell counts with respect to time and a change in the correlation with respect to time are visualized on the screen.

2. The method for displaying cell count information of claim 1, wherein
   the displaying the screen comprises:
      displaying a first graph indicating a change in the first cell count with respect to time, and
      displaying a second graph indicating a change in the second cell count with respect to time, and
   the change in the correlation with respect to time is visualized in accordance with a relationship between the first and second graphs.

3. The method for displaying cell count information of claim 1, wherein
   the displaying the screen comprises:
      displaying at least either a first graph indicating a change in the first cell count with respect to time or a second graph indicating a change in the second cell count with respect to time, and displaying a third graph indicating a change in an indicator with respect to time, the indicator being calculated on the basis of the first and second cell counts and indicating a difference in image recognition performance between the first and second counting models, and the change in the correlation with respect to time is visualized by the third graph.

4. The method for displaying cell count information of claim 3, wherein the displaying at least either the first graph or the second graph comprises displaying the first graph.

5. The method for displaying cell count information of claim 1, wherein the first and second counting models are each a machine learning model.

6. The method for displaying cell count information of claim 5, wherein
the cells are first cells,
the first counting model is a trained machine learning model that has been trained using, as teacher data, an image of cells of the same type as the first cells, and
the second counting model is a trained machine learning model that has been trained using, as teacher data, an image of cells of the same type as the first cells and an image of cells of a different type from the first cells.

7. The method for displaying cell count information of claim 1, wherein the cell images are images of culture cells within a culture container disposed in an incubator.

8. The method for displaying cell count information of claim 1, wherein
the displaying the screen comprises displaying, on the screen, an abnormality in an culture environment for the cells that is decided on the basis of the change in the correlation with respect to time, an abnormality in image recognition based on at least either of the first and second counting models, or an abnormality cause that is a combination of the abnormality in the culture environment and the abnormality in image recognition.

9. The method for displaying cell count information of claim 1, further comprising displaying a cell image obtained at a time corresponding to a selected position on the screen.

10. A method for displaying cell count information, the method comprising:
obtaining a plurality of cell images generated by successively imaging cells;
obtaining a first cell count output by applying each of the plurality of cell images to a first counting model, the first counting model being for counting a number of cells included in an image, and having a higher precision than a second counting model and a lower recall factor than the second counting model;
obtaining a second cell count output by applying, to the second counting model, each of a plurality of cell images that are the same as the images for which the first cell count has been obtained, the second counting model being for counting a number of cells included in an image; and
reporting an abnormality occurrence to a user when an abnormality in a culture environment is detected on the basis of a relationship between the first and second cell counts;
wherein the first and second counting models are each a machine learning model.

11. The method for displaying cell count information of claim 10, further comprising displaying, on a display apparatus, a cell image captured at an image capturing time for which it has been detected that an abnormality occurred thereat.

12. A system comprising:
an electric circuit, wherein the electric circuit is configured to:
obtain, from an image capturing apparatus, a plurality of cell images generated by successively imaging cells,
obtain a first cell count output by applying each of the plurality of cell images to a first counting model, the first counting model being for counting a number of cells included in an image, and having a higher precision than a second counting model and a lower recall factor than the second counting model,
obtain a second cell count output by applying, to the second counting model, each of a plurality of cell images that are the same as the images for which the first cell count has been obtained, the second counting model being for counting a number of cells included in an image, and
cause, on the basis of the first cell count and the second cell count, a display apparatus to display a screen on which at least either of the first and second cell counts and a correlation between the first and second cell counts are visualized;
wherein the electric circuit causes the display apparatus to display the screen on the basis of a first-cell-count history including a plurality of first cell counts corresponding to the plurality of cell images and a second-cell-count history including a plurality of second cell counts corresponding to the plurality of cell images, and
a change in at least either of the first and second cell counts with respect to time and a change in the correlation with respect to time are visualized on the screen.

13. The system of claim 12, wherein
the screen includes
a first graph indicating a change in the first cell count with respect to time, and
a second graph indicating a change in the second cell count with respect to time, and
the change in the correlation with respect to time is visualized in accordance with a relationship between the first and second graphs.

14. A system comprising:
an electric circuit, wherein the electric circuit is configured to:
obtain, from an image capturing apparatus, a plurality of cell images generated by successively imaging cells,
obtain a first cell count output by applying each of the plurality of cell images to a first counting model, the first counting model being for counting a number of cells included in an image, and having a higher precision than a second counting model and a lower recall factor than the second counting model,
obtain a second cell count output by applying, to the second counting model, each of a plurality of cell images that are the same as the images for which the first cell count has been obtained, the second counting model being for counting a number of cells included in an image, and
report an abnormality occurrence to a user when detecting an abnormality in a culture environment on the basis of a relationship between the first and second cell counts;
wherein the first and second counting models are each a machine learning model.

15. The system of claim 14, wherein
the electric circuit displays, on a display apparatus, a cell image captured at an image capturing time for which it has been detected that an abnormality occurred thereat.

16. A non-transitory computer-readable medium having recorded therein a program for causing a computer to perform a process for:
- obtaining a plurality of cell images generated by successively imaging cells from an image capturing apparatus;
- obtaining a first cell count output by applying each of the plurality of cell images to a first counting model, the first counting model being for counting a number of cells included in an image, and having a higher precision than a second counting model and a lower recall factor than the second counting model;
- obtaining a second cell count output by applying, to the second counting model, each of a plurality of cell images that are the same as the images for which the first cell count has been obtained, the second counting model being for counting a number of cells included in an image; and
- on the basis of a first cell count output by inputting the cell images to the first counting model and a second cell count output by inputting the cell images to the second counting model, displaying a screen on which at least either of the first and second cell counts and a correlation between the first and second cell counts are visualized;
- the displaying the screen comprises displaying the screen on the basis of a first-cell-count history including a plurality of first cell counts corresponding to the plurality of cell images and a second-cell-count history including a plurality of second cell counts corresponding to the plurality of cell images, and
- a change in at least either of the first and second cell counts with respect to time and a change in the correlation with respect to time are visualized on the screen.

* * * * *